United States Patent [19]

Ochodnicky et al.

[11] 4,027,516
[45] June 7, 1977

[54] VISCOMETER SYSTEM

[75] Inventors: Samuel Steven Ochodnicky, Dearborn Heights; Frank Joseph Bianchi, Jr., Redford Township, both of Mich.

[73] Assignee: Gam Rad, Inc., Detroit, Mich.

[22] Filed: Mar. 16, 1976

[21] Appl. No.: 667,528

[52] U.S. Cl. .................................................. 73/57
[51] Int. Cl.² ...................................... G01N 11/12
[58] Field of Search .................................... 73/57

[56] References Cited

UNITED STATES PATENTS

| | | |
|---|---|---|
| 3,277,916 | 10/1966 | Deming .............................. 73/57 X |
| 3,304,765 | 2/1967 | Norcross ............................... 73/57 |

*Primary Examiner*—Richard C. Queisser
*Assistant Examiner*—Joseph W. Roskos
*Attorney, Agent, or Firm*—Harness, Dickey & Pierce

[57] ABSTRACT

A viscometer system for providing an indication of the viscosity of a fluid and operable on the falling slug principle and providing a means for providing an output indicative of viscosity as a function of elapsed time.

9 Claims, 6 Drawing Figures

VISCOMETER SYSTEM

SUMMARY BACKGROUND OF THE INVENTION

The present invention relates to apparatus for measuring viscosity and more particularly to improvements in viscometers utilizing the falling slug principle.

There are various known types of apparatus utilized in the measurement of viscosity and which utilize different principles of operation. Thus there are devices utilizing ultrasonics, vibrating reed, rotary cone, etc., to provide a measure of viscosity.

The present invention is an improved viscometer utilizing the falling slug principle. This principle recognizes that the length of time required for a cylindrical slug to fall a given distance through a fluid in a vertical tube is proportional to the viscosity of the fluid.

As will be seen the improved viscometer of the present invention operates on samples taken from a fluid line and can operate automatically to continuously measure the viscosity of new samples. To provide consistency of measurement, the apparatus first circulates the sample until it attains a temperature within a selected temperature range. In this way all measurements on successive samples will be at the same temperature. Where the temperature of the fluid line is maintained the same, then the circulating step previously noted can be eliminated.

In the present invention the system provides essentially a solid state control system. An electrical signal is provided and stored which is an indication of elapsed time and hence of viscosity. This signal is utilized to provide a visual output such as on a pen recorder. With prior constructions the elapsed time relationship is provided by driving a synchronous motor for the elapsed time with a pen being driven through a suitable gear box. The total travel of the pen is dependent upon the number of revolutions of the motor. To change ranges significantly the gear ratio is required to be changed. In the present electronic system, electrical adjustment means are provided whereby the range, the span and zero can all be set to provide utility for a wide range of viscosities.

In addition the mechanical system provides continuous oscillation between zero and final reading making comparison of successive viscosity readings difficult. In the present invention the last reading is stored and the pen held at that recording position until the next reading modifies the stored reading. In this way the recorded information does not continuously return to zero but provides a series of readings which can be readily compared.

The system also provides an overtime signal in the event a cycle is not completed within a selected time interval which would be indicative of a malfunction. In this event the system is placed and held in a purge phase (to be described).

Therefore it is an object of the present invention to provide an improved viscometer system including solid state controls.

It is another object of the present invention to provide an improved viscometer having electrically adjustable means for modifying calibration, the span, and/or zero set.

It is still another object of the present invention to provide an improved viscometer having means for holding the prior signal and maintaining the recorded read out at the magnitude until the next sample is taken.

other objects, features, and advantages of the present invention will become apparent from the subsequent description and the appended claims, taken in conjunction with the accompanying drawings, in which:

GENERAL DESCRIPTION

Figures 1, 2, 2A:
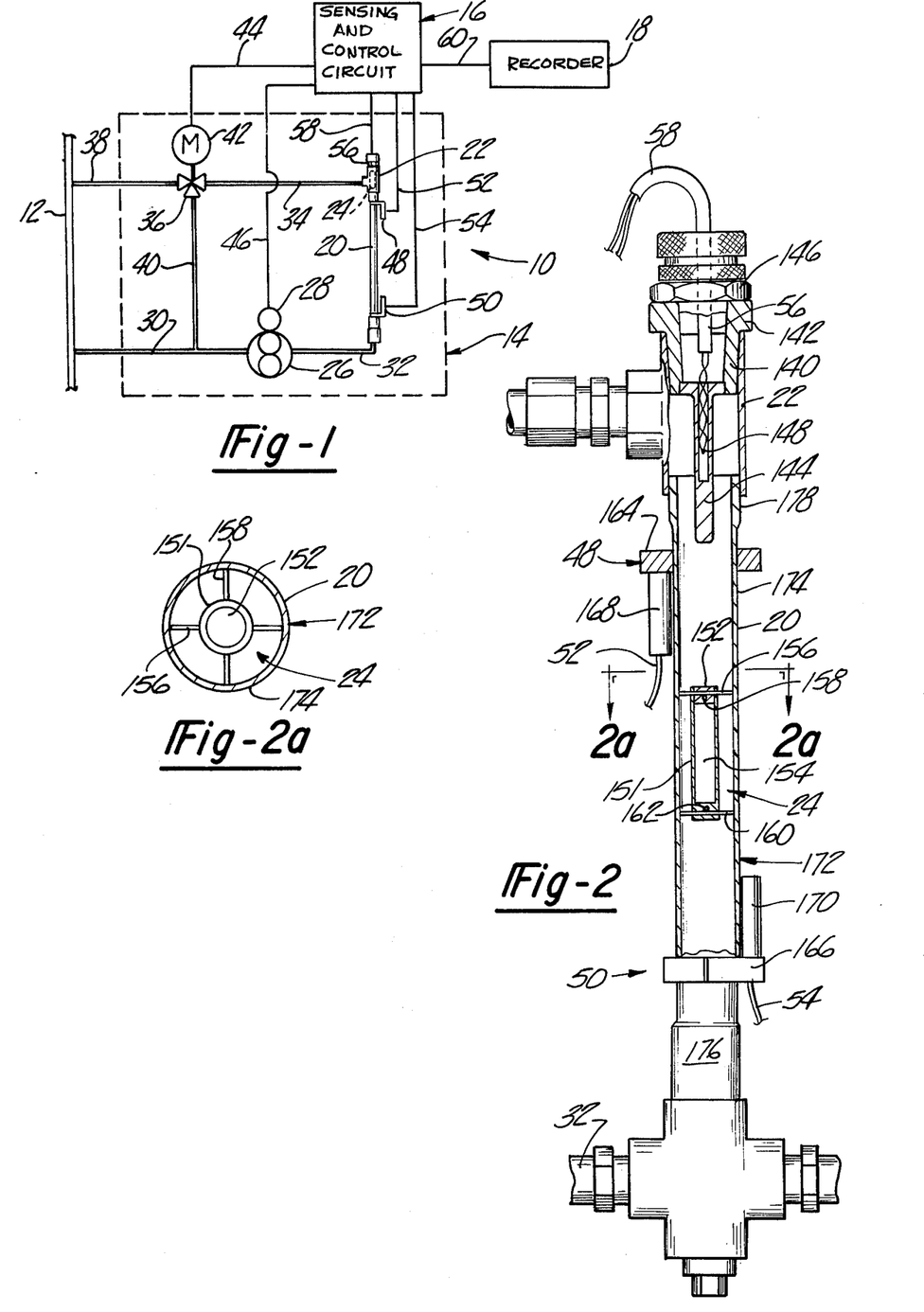
FIG. 1 is a partial mechanical and electrical schematic diagram, with some parts shown in block diagram form, of a system including features of the present invention.
FIG. 2 is an elevational view, with some parts broken away and parts shown in sections depicting the fall tube assembly of the system of FIG. 1.
FIG. 2A is a sectional view of the apparatus of FIG. 2 taken along the line 2A—2A.

Looking now to FIG. 1, a viscometer system 10 is shown in operable relationship with a fluid line 12. The fluid line 12 can be a part of a process stream and carries fluid for the process; the viscosity of the fluid carried is to be monitored, in a manner to be described, by the system 10.

The system 10 includes an Operating Section 14 (shown enclosed in dashed lines) and a Sensing and Control Circuit 16 operable with the Operating Section 14. A Recorder 18 is connected to Circuit 16 and provides a visual display and record of the output as an indication of viscosity.

The Operating Section of System 10 includes an elongated fall tube 20. The fall tube 20 is vertically mounted and has an enlarged portion 22 which serves a purpose to be described.

A cylindrical slug 24 is located in clearance relationship in the fall tube 20 and can fall by force by gravity from its uppermost position near the enlarged portion 22 to the bottom of the tube 20. As will be seen, the time for descent of the slug 24 is measured and provides an indication of the magnitude of the viscosity of the fluid in the tube 20.

Fluid from the process line 12 is pumped into the fall tube 20 via a gear pump 26 which in turn is powered by an electric motor 28. A conduit 30 connects the inlet of the pump 26 to the process line 12 while a conduit 32 connects the output of pump 26 to the lower end of the tube 20. A fluid circuit back to the line 12 is completed by means of a conduit 34 connected between the upper, enlarged portion 22 of fall tube 20 and the inlet of a three way valve 36. A conduit 38 connects the outlet of valve 36 to the process line 12. The outlet conduit 38 is connected upsteam of the inlet conduit 30. A bypass conduit 40 is also connected between the outlet of valve 36 and the inlet of pump 26. The valve 36 is a threeway valve actuated between two positions by an electric motor 42. In the first position, the valve 36 places conduits 34 and 38 in fluid communication while blocking conduit 40; in the second position, the valve 36 connects conduit 34 with bypass conduit 40 while blocking conduit 38. The valve 36 is actuated by the motor 42 which in turn is selectively energized by the Sensing and Control Circuit 16 via electrical line 44. In a similar manner the motor 28 for pump 26 is selectively energized by the Sensing and Control Circuit 16 via electrical line 46.

As noted the viscosity of the fluid in fall tube 20 is determined by the elapsed time for the slug 24 to fall. The elapsed time is measured over a preselected distance which is selectively determined by upper and lower magnetic switches 48 and 50, respectively. The switches 48 and 50 can be reed switches and are selectively movable located along fall tube 20 a predetermined distance part. The switches 48 and 59 are electrically connected with the Sensing and Control Circuit 16 via lines 52 and 54, respectively. In addition, a temperature responsive resistor or thermistor 56 is located in the enlarged portion 22 and senses the temperature of the fluid in the fall tube 20; the thermistor 56 is connected to the Sensing and Control Circuit 16 via line 58.

DESCRIPTION OF OPERATION

As will be seen, the Sensing and Control Circuit 16 provides means for automatic, continuous cycling or manual cycling. The automatic cycling will be described first.

The system 10 has three operative phases (a) purge phase, (b) recirculate phase, and (b) measure phase.

When the System 10 is first actuated, it automatically is placed in the purge phase. In this condition, the valve 36 is placed in its first position connecting the fall tube 20 to the process line 12 via conduits 34 and 38; at the same time bypass conduit 40 is blocked. In the purge phase, any fluid from a previous measuring cycle is returned to the process line 12 while a new sample of fluid is pumped in via conduit 30. At the end of a measuring cycle the slug 24 will have fallen near the bottom of the tube 20 proximate the switch 50. The slug 24 will not fall past switch 50 but will be carried up to the enlarged portion 22 of the tube 20 of the force of the velocity of the incoming fluid. The purge phase will continue until the temperature sensed by thermistor 56 attains a preselected high temperature at or near the temperature of the fluid in the process line 12. When this high temperature is attained the Sensing and Control Circuit switches the System 10 into the second or recirculate phase.

When switched to the recirculate phase, the motor 42 is energized to actuate the valve 36 to its second position communicating bypass conduit 40 with fall tube 20 via conduit 34 while blocking flow to outlet conduit 38. In this phase or condition the pump 26 simply recirculates the new sample of fluid now trapped in the fluid circuit including the fall tube 20, the conduits 34, 40 and 32. As recirculation continues the fluid is cooled until it attains a preselected low temperature as sensed by the thermistor 56. When this temperature is reached, the Sensing and Control Circuit 16 switches the System 10 to the third or measure phase. The purpose of the recirculate phase is to bring the temperature of each new cycle of fluid to a known, desired temperature. This assures a uniformity of test or measure condition.

When switched to the measure phase, the valve 36 is maintained in its recirculate phase condition; however, the motor 28 for pump 26 is de-energized thereby deactuating the pump 26. With the pump 26 off, fluid is no longer being circulated in fall tube 20 and hence the slug 24 can now drop from its uppermost position. As the slug falls past magnetic switch 48 a timing circuit in Sensing and Control Circuit 16 is actuated initiating the timing operation. When the slug 24 falls past the second switch 50 the timing circuit is actuated to cease the timing operation. At the same time, the Sensing and Control Circuit 16 places the System 10 back in its original or purge phase and the cycle is repeated.

The elapsed time for the fall of the slug 24 to actuate switches 48 and 50 provides an indication of the magnitude of the viscosity of the fluid sample in fall tube 20. This signal or indication can be transmitted to a display such as Recorder 18 via line 60.

SENSING AND CONTROL CIRCUIT 16

Figure 3:
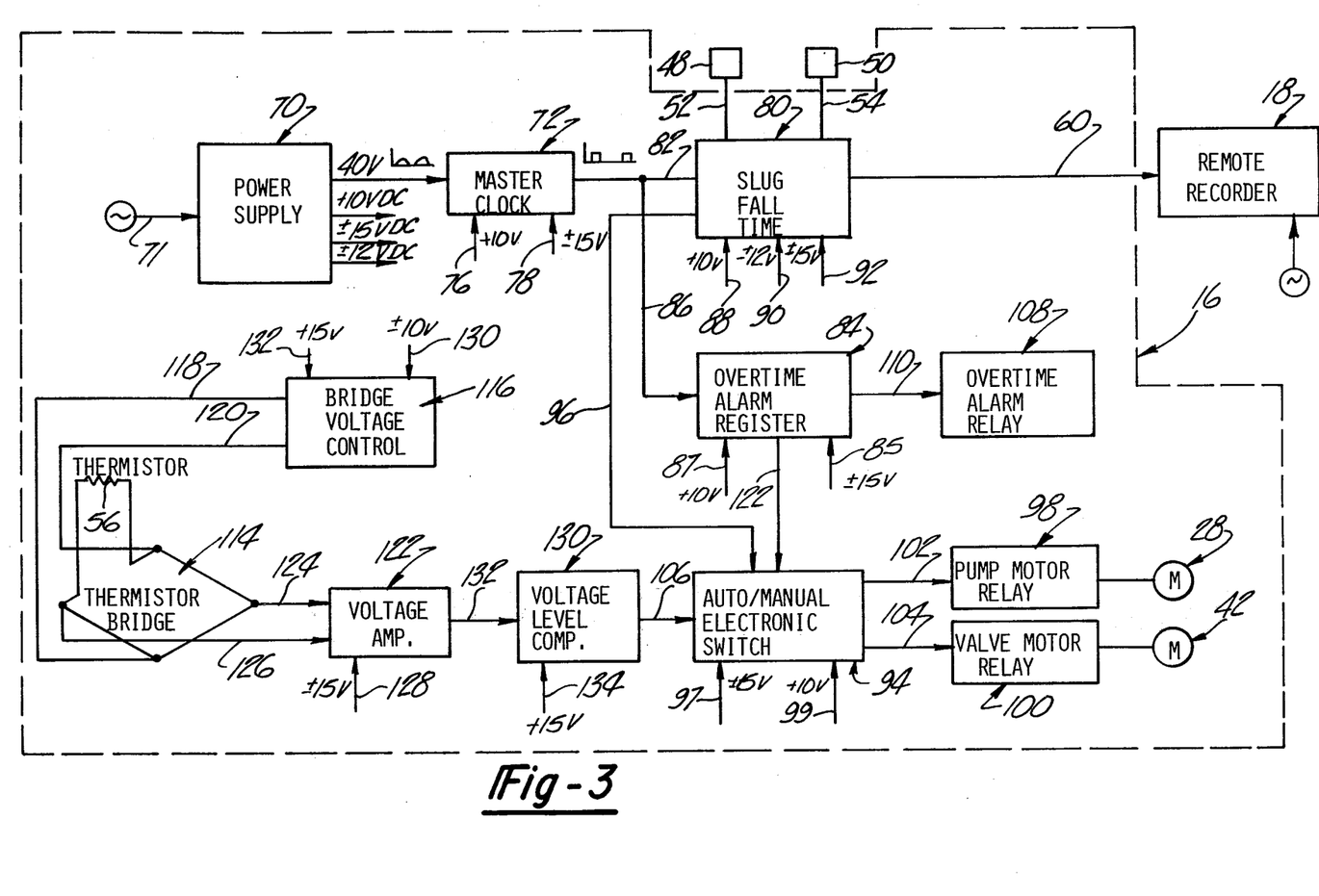
FIG. 3 is a block diagram of a sensing and control circuit section of the system of FIG. 1.

A block diagram of the Sensing and Control Circuit 16 is shown in FIG. 3. The Circuit 16 includes a power supply 70 which is energized from a conventional sixty cycle 115 volt a-c source via line 71. The power supply 70 provides a direct current output which appears as +10 volts, +15 volts, +15 volts, +12 volts, and −12 volts. In addition the supply 70 provides a half wave rectified pulsating direct current voltage of 40 volts peak. For purposes of simplicity, the voltage output lines from supply 70 are not shown completed to each associated circuit; however, where the input to each such circuit is shown with a voltage designation it is understood that such input is received from the power supply 70.

The power supply 70 provides a 60 cycle, 40 volt half wave signal to a master clock section 72 via a line 74. The clock 72 is a digital clock and also received d-c voltages from supply 70 via lines 76 and 78, all as indicated on the drawing. The master clock performs a frequency dividing function such that it has a square wave output frequency of 10 cycles per second. This output signal is transmitted to a slug fall time section 80 via line 82 and to an overtime alarm register section 84 via conductor 86. Section 84 receives d-c voltages from the supply 70 via lines 85 and 87. The slug fall time section receives d-c voltages from supply 70 via lines 88, 90 and 92. At the same time section 80 also receives the signals from reed switches 48 and 50 via lines 52 and 54, respectively. Thus as the slug 24 passes and actuates switch 48 a signal is transmitted via line 52 to slug fall time section 80 to initiate timing. As the slug 24 continues its descent it passes and actuates switch 50 and a signal is transmitted via line 54 to cease timing. The slug fall time section 80 provides a signal indicating the magnitude of that elapsed time as a function of the number of pulses received via line 82. This elapsed time signal is stored in section 80 and at the same time transmitted to the recorder via line 60. The recorder 18 also receives power from the 115 volt a-c source. The recorder 18 can be of a pen recorder of a round chart type such as Model 4331-20A manufactured by Bristol Instruments. It is significant that the slug fall time section 80 stores the elapsed time signal and, until that signal is changed by a new reading, transmits the same to the recorder 18. Thus recorder 18 will provide a recorded output display on a chart having a magnitude as a function of elapsed fall time which can be readily correlated to a magnitude of viscosity. Since the recorder 18 continuously receives the stored elapsed time signal, it will provide a continuous display of this signal and succeeding signals. This provides for a more obviously observable indication of a change in viscosity as contrasted to a system in which the signal to a recorder drops to zero between successive readings.

The slug fall time section 80 also provides the signal from reed switch 50 to electronic switch section 94 via line 96. The switch section 94 receives d-c voltage from supply 70 via lines 97 and 99 and functions in a manner to be seen.

As will be seen, the electronic switch 94 has two modes of operation an "automatic" mode and a "manual" mode. In the automatic mode the switch 94 will automatically switch the System 10 through its three phases of operation, i.e. purge, recirculate, and measure. In the manual mode, switch 94 can be actuated to permit the operator to select any mode and maintain that mode for as long as desired. Energization of motors 28 and 42 are controlled by relays 98 and 100, respectively, which in turn are controlled by electronic switch 94 via conductors 102 and 104, respectively. As previously indicated, when in the automatic mode, the System 10 will be switched in sequence from one phase to the next in response to temperature and time signals.

Thus the electronic switch 94 operates in response to temperature related signals received via line 106. Switch 94 also receives a time related signal from the slug fall time section via line 96. Thus when the measurement phase is completed, i.e. slug 24 actuated lower switch 50, the switch 94 will be actuated to energize the pump motor relay 98 and valve motor relay 100 to place System 10 in the purge phase. The purge phase will be continued until an appropriate signal from line 106 indicates that the temperature of the fluid has reached a selected high temperature. At this time switch 94 operates on valve motor relay 100 to place the valve 42 in its second position whereby the recirculation phase is initiated. This phase continues until the fluid sample cools to a selected lower temperature, the attainment of which results in another signal via line 106 whereby switch 94 operates on pump motor relay 98 to place the System 10 in the measure phase upon the completion of which the cycle repeats itself.

The complete cycle of the System 10 is timed via overtime alarm register 84 and if the elapsed time for any cycle exceeds a preselected time interval a pair of signals are generated. A first signal is transmitted to an overtime alarm relay 108 via line 110 to provide a visual or audio alarm to the operator that the selected elapse time has passed and that there is a possible malfunction in the System 10, or for that matter, a problem exists in the process line 12. A second signal is transmitted to switch 94 via line 122 in response to which switch 94 places and holds the System 10 in the purge phase of operation. This feature is designed to minimize the possiblity of freeze up of the fluid within the system in the event of a malfunction.

As noted the switch 94 receives temperature signals via line 106; these signals are generated as a result of changes of resistance of thermistor 56. Thermistor 56 defines one leg of a conventional bridge circuit 114. A bridge voltage control section 116 is connected across opposite legs of the bridge circuit 114 via lines 118 and 120 and provides an adjustable operational voltage level. The output from bridge circuit 114 is fed to a voltage amplifier 122 via lines 124 and 126. Amplifier 122 receives a d-c voltage from supply 70 via line 128 while the bridge voltage control circuit 116 receives d-c voltages from supply 70 via lines 130 and 132. The amplified temperature signal from amplifier 122 is transmitted to a voltage level comparator section 130 via line 132. The comparator 130 provides the signals to switch 94 upon attainment of the previously described high and low temperatures. Comparator 130 receives d-c voltage from supply 70 via line 134.

FALL TUBE ASSEMBLY

Looking now to FIG. 2 an assembly is shown of the fall tube 20, slug 24, thermistor 56, and switches 48 and 50.

The thermistor 56 includes a two piece stainless steel housing 140 having an internally and externally threaded hollow plug portion 142 and an elongated hollow nose portion 144 secured to the lower end thereof. A threaded cap 146 has a thermistor element 148 secured thereto and is threadably secured to the internally threaded portion of plug portion 142. Line 58 is connected to thermistor element 148 and locates the element within the cavity of nose portion 144 and extends outwardly from cap 146. The cavity defined by portions 142 and 144 is sealed by conventional means. The thermistor 56 is threadably secured to the enlarged portion to define a fluid tight seal and locates the nose portion 144 with the thermistor element 148 in the fall tube 20.

The slug 24 comprises a hollow stainless steel cylinder 151 made up of an elongated tube 150 open at one end and a cap 152 sealingly closing that one end. An Alnico permanent magnet 154 is encapsulated within the cylinder 151 and provides the magnetic field necessary to actuate the magnetically responsive reed switches 48 and 50. A pair of guide rods 156 and 158 are located in quadrature with each other and extend through and outwardly from the capped end of the cylinder 151. Guide rods 160 and 162 are similarly located at the opposite end. The guide rods 156, 158, 160 and 162 are of a length slightly less than the inside diameter of the fall tube 20 and guide the slug 24 as it moves vertically upwardly and downwardly in the fall tube 20.

The magnetic reed switches 48 and 50 are similar in structure and are selectively, movably located along the length of fall tube 20 via releasable clamping rings 164 and 166, respectively. Note that vertically extending body portions 168 and 170 house the switch elements for switches 48 and 50, respectively. With the structure shown the switches can not only be moved vertically towards or away from each other but can also be rotated to move the body portions 168 and 170 out of alignment with each other and hence permit close vertical location of the switches 48 and 50.

Note that the fall tube 20 includes an elongated tube member 172. The member 172 is constructed of a seamless stainless steel tube. The center portion 174 is machined down to a smaller outside diameter leaving enlarged diameter portions 176 and 178 at opposite ends; these ends are appropriately threaded with a standard thread for threaded connection to associated apparatus. The wall thickness of the tube member 172, then, has been reduced. This improves the magnetic field strength received by the switches 48 and 50 from the slug 24 and hence provides greater assurance of reliable switch actuation. In a preferred form of the invention a standard tube having an outside diameter of 1.315 inch and inside diameter of 1.049 inch was reduced in O.D. to approximately 1.250 inch thus providing the reduced diameter portion 174 with a wall thickness of approximately 0.100 inch (reduced from the normal thickness of 0.133 inch at the larger end portions 176, 178).

Note that slug 24 as guided by the associated rods has ample clearance with the inside wall of tube 176 whereby the flow of fluid therearound will be generally unrestricted. The nose portion 144 of thermistor 56 provides a stop for the slug 24 at its uppermost position.

SCHEMATIC DESCRIPTION OF SENSING AND CONTROL CIRCUIT 16

Figure 4A:
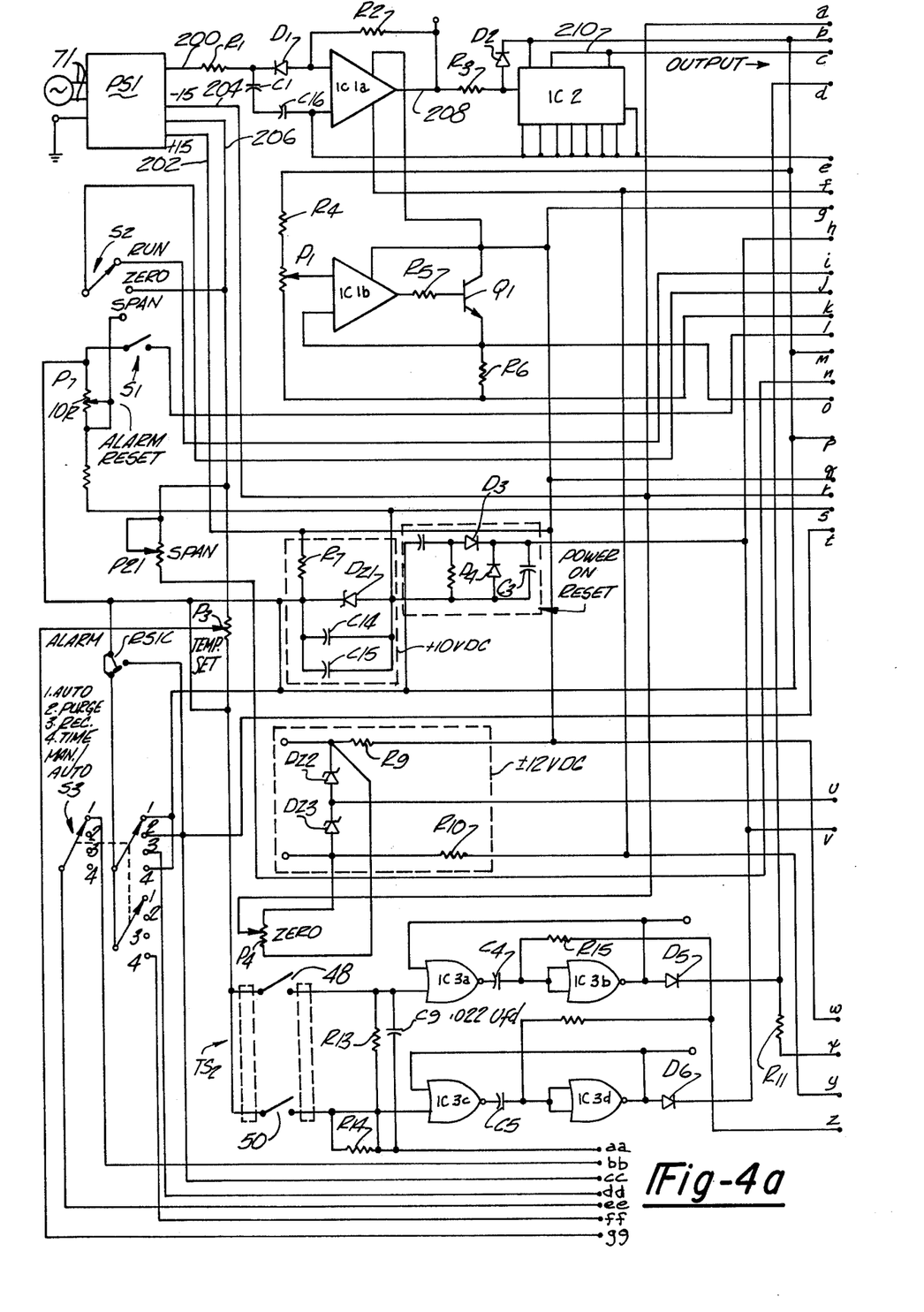
FIGS. 4A and 4B depict an electrical schematic diagram of portions of the control circuit section of FIG. 3.
Figure 4B:
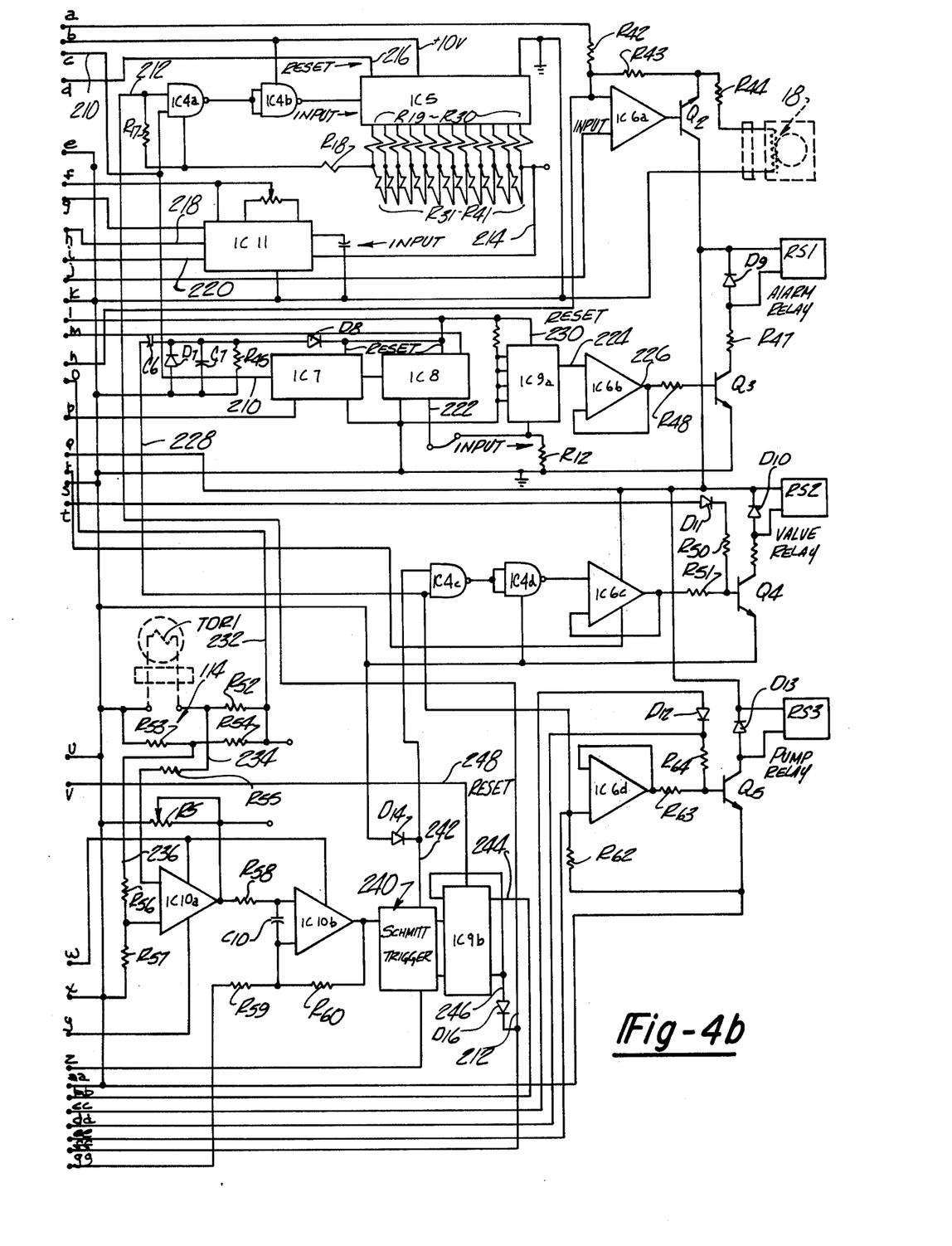

The schematic diagram for the sensing and control circuit 16 is shown in FIG. 4A and 4B. It should be understood that the block diagram of FIG. 3 was for purposes of simplicity and that some of the components of FIGS. 4A and 4B may serve functions in more than one of the sections of FIG. 3.

In FIGS. 4A and 4B the power supply 70 includes voltage supply PSI which receives 120 volt 60 cycle a-c from a source and provides at conductor 200 a 40 volt peak to peak a-c voltage. A +15 volt DC supply is provided at conductor 202 while −15 volts are provided at conductor 204. Conductor 206 defines the system ground. A +10 volt DC voltage is provided by the network including zener diode DZ1, capacitor C14 and C15 and current limiting resistor R7. A +12 volt and −12 volt DC voltage is provided by the network including zeners DZ2 and DZ3 and current limiting resistors R9 and R10.

The System 10 is partly controlled by a Run/Calibrate switch S2 which has three positions, i.e. run, zero, and span. A switch S1 is an alarm reset switch which functions in a manner to be seen. Switch S3 sets the mode of operation and has three separate poles, A, B, C and four positions, the first for setting automatic sequencing through the three phases, and the second, third and fourth for manually selecting the purge phase, the recirculating phase or the time or measure phase. For the purposes of the following discussion it is assumed that switch S2 is in the 'run' position, switch S1 is open, and switch S3 is in the automatic mode.

The a-c output at conductor 200 is rectified via a circuit including a resistor R1 and diode D1. The half wave rectified signal is connected to the input of IC 1a (hereinafter the designation IC shall refer to an integrated circuit structure) which is an operational amplifier utilized as an amplifier and buffer. Note that IC 1b is a structure similar to IC 1a and is integral therewith although independent in function. Capacitors C1 and C16 provide filtering while reistors R1 and R2 affect the gain of IC 1a. The function of IC1a is to provide a more nearly square wave output in response to the sinusoidal half wave input. The output of IC 1a at conductor 208 is a 60 cycle square wave of fixed amplitude and width.

The output at conductor 208 is connected to IC 2 via a current limiting resistor R3. The IC 2 is a 'programmable divide by N counter' which is connected to divide by 6 and hence provide a square wave output at conductor 210 of 10 cycles per second. Diode D2 is connected to the 10 volt DC supply and provides input voltage protection.

The circuits IC4a–d define a 'quad two input nand gate '; each IC 4 structure is independent although in a single integrated circuit structure.

The IC 4a portion is connected as a nand gate with the ten cycle output at conductor 210 connected to one input thereof. The other input is connected via conductor 212 and dropping resistor R17. Thus IC 4a will provide an output signal only when the appropriate two input signals are present via conductors 210 and 212. When this condition exists (as will be described) a signal of 10 pulses per second appears at the output of IC 4a, which output is connected to both inputs of IC 4b. IC 4b then acts solely as in inverter and provides an inverted output whereby the 10 cycle per second signal will again be of the same polarity as that of the input at conductor 210.

The output from IC 4b is connected to the input of IC 5 which is a 12 stage counter. Reistors R19–R30 and R31–R41 are connected as an R-2R resistive network to the outputs of IC 5; this network is connected to ground via reistor R18. Thus the voltage appearing at output conductor 214 will be a sum indicative of the number of pulses transmitted to IC 5 over an elapsed time period. Thus in a sense the R-2R network performs an integrating function. As will be seen the elapsed time is that time required for slug 24 to travel the distance between switches 48 and 50 and hence is an indication of viscosity. The IC 5 will be reset at the beginning of a timing cycle via a signal at conductor 216.

The elapsed time output voltage at conductor 214 is connected to IC 11 which is a sample and hold module. Capacitor C8 is a low leakage long time storage capacitor the charge on which is an indication of the elapsed time voltage at conductor 214. The voltage at C8 will be modified to correspond to changes in voltage at conductor 214 only after the measure phase is completed, i.e. the slug 24 energized lower switch 50. This occurs via a signal at conductor 218 which signal causes IC 11 to function to update the charge at C8 to reflect the most recent elapsed fall time for slug 24. A trim pot P6 provides means for nulling offset voltages of IC 11.

The output from IC 11 is taken from conductor 220 through the switch S2 in the 'run' position and to the input of an amplifier IC6a; IC6a is an independent amplifier portion of an integrated circuit member including IC6b, c, and d. The gain of voltage amplifier IC 6a is determined by resistors R42 and R43. The output from IC 6a is transmitted to the base of an n-p-n transistor Q2 which provides current amplification. A current limiting resistor R44 is connected from the emitter of Q2 to the high voltage side of the pen drive for recorder 18.

Thus recorder 18 will see a current signal having a magnitude related to the charge to capacitor C8. Since the charge is stored and held and not erased between cycles the recorder will provide a continuous display or record of that magnitude until it is modified at the next cycle.

The apparatus can be calibrated by means of span potentiometer P4 and zero potentiometer P4 all connected with switch S2. A potentiometer P7 is preset to provide a known voltage to IC 6a corresponding to a known magnitude of viscosity with the switch S2 in the 'span' position. Next the span potentiometer P2 is manipulated to provide full scale or a desired level on the read out at the recorder 18. Next the switch S2 is switched to the 'zero' position and the zero potentiometer P4 adjusted to provide a zero read out at recorder 18.

As noted, in the event that the elapsed time for a cycle of operation exceeds a given magnitude an overtime relay is actuated. In FIG. 4B this relay is RS1. Timing function is performed by a pair of integrated 12 stage counters IC7 and IC8 (each of which is similar to IC5). The output pulses from IC2 at conductor 210 is connected to the input of IC7. IC7 is connected to IC8 where the range of counting is substantially increased. The output of the combination is provided at conductor 222, which is connected to ground via resistor R12. The output at conductor 222 is connected to the input of IC9a a 'dual JK flip flop'. When an input signal appears at conductor 222, indicating that the preselected elapsed time has been exceeded, then a latched output signal is provided at conductor 224. This signal will remain even though the signal at conductor 222 ceases. The output at conductor 224 is transmitted to IC6b a voltage-follower amplifier, which in turn provides an output at conductor 226 to the base of a current amplifier, n-p-n transistor Q3 via resistor R48. Q3 drives the alarm relay RS1 via resistor R47 and diode D9. In addition to operating the alarm, the System 10 is placed and held in the purge phase of operation via actuation of relay contact RS1C (see FIG. 4A).

The alarm system counters IC7 and IC8 will be reset at the beginning of each purge phase via a reset signal at conductor 228. The signal at conductor 228 is communicated to IC7 and IC8 via a filter network including capacitors C6 and C7, diodes D7 and D8 and resistor R45. The network also provides voltage protection to the circuit. Note that even though counters IC7 and IC8 are reset, IC9a will remain latched once an overtime condition has been sensed. IC9a must be manually reset via actuation of alarm reset switch S1 which places a reset signal on 19a via conductor 230. With IC9a reset, IC6b and Q3 and hence alarm relay RS1 are deactuated.

As previously noted the System 10 functions in response to temperature of the fluid. Thus the bridge circuit 114 includes thermistor TDR1, and resistors R52, R53, and R54. Voltage is applied to the bridge circuit 114 via conductor 232. Conductor 232 obtains a preselected potential from buffer amplifier IC1b which drives n-p-n transistor Q1 via resistor R5. The voltage output can be adjusted via pot P1 relative to resistor R4 with resistor R6 providing a load resistance for the circuit.

The output voltage from bridge 114 appears across conductors 234 and 236. This voltage is transmitted to IC10a, via resistors R56 and R57 and R55; IC10a is connected as a differential amplifier with its gain selectively varied via pot P5.

The output from IC10a is transmitted to IC10b via resistor R58; IC10b is connected as a voltage comparator and has a filter capacitor C10 connected across its input. The second input is connected to a temperature set pot P3 via limiter resistor R59. Thus the high temperature level is set by operation of P3. When the voltage at R58 reaches a preselected level relative to that at R59 from P3 IC10b will be actuated to provide an output signal. Resistor R60 is connected to provide feed back such that when the sensed temperature of the fluid drops to the level which actuated IC10b it will not be deactuated and will require a predetermined, fixed lower temperature to deactuate IC10b. This provides the function previously described whereby recirculate phase will continue until the fluid is cooled to a selected lower magnitude. As noted R60 provides for a fixed differential between the high and low temperatures.

The output from IC10b is connected to the input of a Schmitt trigger circuit 240. The Schmitt trigger provides a sharper output pulse and minimizes possible error. The Schmitt trigger 240 provides an output at conductor 242 for the relay circuit for valve 36. At the same time the Schmitt trigger provides a signal to IC9b a 'dual JK flip flop' (integral with but electrically independent from IC9a). IC9a in response to a signal from trigger 240 will be actuated to a latched condition and has a true output at conductor 244 and an inverse output at conductor 246. Thus when the output at conductor 244 is high that at conductor 246 is low and vice versa. IC9b can be reset via a signal at conductor 248. Thus either a signal from trigger 240 or reset conductor 248 will cause IC9b to flip flop. The reset signal at conductor 248 will be provided either by actuation of the lower switch 50 or by an initial power on condition. The power on circuit comprises capacitors C2 and C3, diodes D3 and D4 and resistor R8.

IC9b provides its true output at conductor 244 which is transmitted via switch S3 to amplifier IC6d. The inverse output at conductor 246 is transmitted via diode D16 to conductor 212 at the input of IC4a. Thus IC4a will permit counting only when the appropriate signal appears at conductor 212. Hence when the temperature of the fluid attains the preselected high temperature the inverse output at conductor 246 will place IC4a in a condition to transmitt pulses from IC2 to counter IC5. At the same time the true signal at conductor 244 will apply a reset signal to overtime alarm counters IC7 and IC8 to restart the counting since a new cycle is being initiated. Also the signal appears at the input of amplifier IC6d.

IC6d controls the pump relay R53 whereby the pump motor 26 is energized. The signal at IC6d, across resistor R62, will provide an output signal across R63 to the base of n-p-n transistor Q5 which will energize relay RS3 and actuate the pump motor 28. Q5 will also be actuated to energize relay RS3 and actuate the pump in the event of an overtime signal. This occurs by actuation of relay contact RSIC which brings Q5 on via diode D12 and resistor R64. Q5 can also be energized by placing switch S3 in the purge or recirculate position.

When the temperature drops to the selected low level IC9b will be actuated to deactuate IC6d whereby the pump 26 will be deactuated and the slug 24 can fall and the measure phase begins.

The last function is the determination of the measure interval. Switches 48 and 50 are shown as a part of switch TS2. Switches 48 and 50 function with "quad two input nor gates" IC3a, b, c and d. These are connected to operate as a single shot circuit providing a single pulse of a predetermined magnitude and width.

Switch 48 is actuated as slug 24 passes it on its descent. S48 is connected to the input of IC3a and its closure will actuate it to provide a signal to IC3b via capacitor C4. IC3b acts as an inverter with resistor R15 affecting the input. The output pulse from IC3b is transmitted via diode D5 and resistor R11 to counter IC5 via conductor 216 to reset that counter so that it will now provide a count of the elapsed fall time. When lower switch 50 is actuated by slug 24 it will be closed to actuate IC3c which will provide a signal to IC3d via capacitor C5. IC3d acts as an inverter of the signal and operates with resistor R16. The output is transmitted via diode D6 to Storage and Hold IC11 whereby IC11 is actuated to sample the voltage at conductor 214 and modify the charge on C8 to indicate the new elapsed time or viscosity. At the same time the signal through D6 is transmitted to IC9b via conductor 248 to reset that circuit whereby the counting function of IC4c is interrupted holding the counting circuit from counting whereby IC11 and capacitor C8 will see only the elapsed time signal at conductor 214. Switch 50 is connected to resistor R14 while switch 48 is connected to resistor R13 and capacitor C9. The circuits of IC3-a—d provide definite signals and avoid error which might result from contact chatter.

The valve relay RS2 is controlled by a circuit including IC4c and IC4d which are a part of the "quad two input Nand gate" which includes IC4a and IC4b although each IC functions independently except where externally interconnected. IC4c receives two inputs one from the Schmitt trigger 240 indicating the attainment of the temperature condition and the other from IC9b also indicating the temperature condition. When the temperature is at the high level the IC4c will be actuated to place valve relay RS2 to recirculate; when it is low it will be placed in purge from recirculate until the lower switch 50 is actuated indicating the end of the measure phase; this is accomplished via the reset of IC9b. Note that the condition of valve 36 is the same for recirculate and measure. Thus after the measure cycle the reset of IC9b places valve 36 in the purge phase and at the same time the pump relay RS3 is energized via IC9b to actuate the pump 26.

The IC4d is an inverter and provides its output to amplifier IC6. The output of IC6c is transmitted to the base of n-p-n transistor Q4 via resistor R51. Q4 actuates relay RS2 via resistor R49 which is connected to diode D10. Q4 can be actuated manually via switch S3 via diode D11 and resistor R50.

In a preferred form of the invention the above identified components of circuit 4A and 4B are as follows:

| SYMBOL | DESCRIPTION | MANUFACTURER* | MANUFACTURER P/N* |
| --- | --- | --- | --- |
| C1 & 2 | Capacitor 1.0 µfd | | |
| C3–C5 | Capacitor .001 µfd | | |
| C6 | Capacitor .1 µfd | | |
| C7 | Capacitor .001 µfd | | |
| C8 | Capacitor 1 µfd | | |
| C9 | Capacitor .022 µfd | | |
| C10 | Capacitor 1 µfd | | |
| C11 | Capacitor .47 µfd | | |
| C12–C13 | Capacitor .47 µfd | | |
| C14 | Capacitor 1 µfd | | |
| C15 | Capacitor .001 µfd | | |
| C16 | Capacitor 1.0 µfd | | |
| D1 | Diode | Motorola | IN4002 |
| D2–D8 | Diode | G.E. | IN914A |
| D9–D10 | Diode | Motorola | IN4002 |
| D11 | Diode | G.E. | IN914A |
| D12 | Diode | Motorola | IN4002 |
| D13–D16 | Diode | G.E. | IN914A |
| D17–D18 | Varistor Metal Oxide | G.E. | V130LAZ |
| DZ1 | Diode, Zener 10V | Motorola | IN5347B |
| DZ2–DZ3 | Diode, Zener 12 V | Motorola | IN5349B |
| IC1 | Intergrated Circuit | RCA | CA747E |
| IC2 | Intergrated Circuit | RCA | CD4018AE |
| IC3 | Intergrated Circuit | RCA | CD4001AE |
| IC4 | Intergrated Circuit | RCA | CD4011AE |
| IC5 | Intergrated Circuit | RCA | CD4040AE |
| IC6 | Intergrated Circuit | National | LM224 D |
| IC7–IC8 | Intergrated Circuit | RCA | CD4040AE |
| IC9 | Intergrated Circuit | RCA | CD4013AE |
| IC10 | Intergrated Circuit | RCA | CD747E |
| IC11 | Sample & Hold Module | Burr Brown | SHO 23 ET |
| P1 | Potentiometer, 5K | | |
| P2 | Potentiometer, 100K | | |
| P3 | Potentiometer, 10K | | |
| P4 | Potentiometer, 20K | | |
| P5 | Potentiometer 1M | | |
| P6 | Potentiometer 10K | | |
| P7 | Potentiometer 10K | | |
| Q1–Q5 | Transistor | Fairchild | 2N3567 |
| R1–R2 | Resistor 10K | | |
| R3 | Resistor 2K | | |
| R4 | Resistor 10K | | |
| R5 | Resistor 4.7K | | |
| R6 | Resistor 10K | | |
| R7 | Resistor 100Ω | | |
| R8 | Resistor 100K | | |
| R9–R10 | Resistor 100Ω | | |
| R11–R12 | Resistor 50K | | |
| R13–R15 | Resistor 100K | | |
| R16 | Resistor 10M | | |
| R17–R30 | Resistor 100K | | |
| R31–R41 | Resistor 50K | | |
| R42 | Resistor 100K | | |
| R43 | Resistor 50K | | |
| R44 | Resistor 470Ω | | |
| R45–R46 | Resistor 100K | | |
| R47 | Resistor 5Ω | | |
| R48 | Resistor 200Ω | | |
| R49 | Resistor 5Ω | | |
| R50 | Resistor 680Ω | | |
| R51 | Resistor 220Ω | | |
| R52–R54 | Resistor 100K | | |
| R55–R56 | Resistor 3.3K | | |
| R57 | Resistor 470K | | |
| R58–R59 | Resistor 33K | | |
| R60 | Resistor 10M | | |
| R62 | Resistor 100K | | |

-continued

| SYMBOL | DESCRIPTION | MANUFACTURER* | MANUFACTURER P/N* |
|---|---|---|---|
| R63-R64 | Resistor 1K | | |
| R67 | Resistor 10K | | |
| R68 | Resistor 50K | | |

*Or Equivalent

Thus it can be seen that the above provides an improved viscometer having improved reliability and function.

While it will be apparent that the preferred embodiments of the invention disclosed are well calculated to fulfill the objects above stated, it will be appreciated that the invention is susceptible to modification, variation and change without departing from the proper scope or fair meaning of the invention.

What is claimed is:

1. A viscometer system operable with a process line carrying a fluid to be measured and comprising a vertically mounted fall tube, a slug located in said fall tube for movement therein between upper and lower positions, pump means for pumping fluid into said fall tube, valve means operable to a plurality of conditions for directing flow of fluid from said fall tube, conduit means connecting said pump means, said valve means, said fall tube and the process line, actuating means operably connected with said fall tube, said pump means, said valve means and said conduit means for automatically, sequentially placing the system in the following phases of operation: (a) purge phase in which said valve means is conditioned such that fluid is pumped by said pump means from the process line, through said fall tube, and through said valve means back to the process line, (b) recirculate phase in which said valve means is conditioned such that fluid flow to the process line is blocked and fluid is recirculated in a fluid circuit comprising said fall tube, said valve means, said conduit means and said pump means, and (c) measure phase in which said pump means is deactuated while the remaining portions of the system are in said recirculate phase and said slug can fall, and timing means for providing a voltage output having a magnitude varying in accordance with the variations in the elapsed time for said slug to fall a selected distance, said timing means comprising a pair of magnetically actuated switches connected to said fall tube, each of said switches being independently movably mounted and capable of variation in both vertical and circumferential location.

2. The apparatus of claim 1 with said fall tube being of a reduced wall thickness at the location of said switches whereby the sensitivity of said switches is improved.

3. A viscometer system operable with a process line carrying a fluid to be measured and comprising a vertically mounted fall tube, a slug located in said fall tube for movement therein between upper and lower positions, pump means for pumping fluid into said fall tube, valve means operable to a plurality of conditions for directing flow of fluid from said fall tube, conduit means connecting said pump means, said valve means, said fall tube and the process line, actuating means operably connected with said fall tube, said pump means, said valve means and said conduit means for automatically, sequentially placing the system through repeated cycles in the following phases of operation: (a) purge phase in which said valve means is conditioned such that fluid is pumped by said pump means from the process line, through said fall tube, and through said valve means back to the process line, (b) recirculate phase in which said valve means is conditioned such that fluid flow to the process line is blocked and fluid is recirculated in a fluid circuit comprising said fall tube, said valve means, said conduit means and said pump means, and (c) measure phase in which said pump means is deactuated while the remaining portions of the system are in said recirculate phase and said slug can fall, an electrically responsive master clock means for providing a plurality of square wave signals at a preselected frequency, slug fall time means for receiving said square wave signals and providing an elapsed time voltage output in response thereto with said elapsed time voltage output having a magnitude varying in accordance with the variations in the elapsed time for said slug to fall a selected distance, overtime alarm register means receiving said square wave signals from said master clock means and providing an alarm signal in response to an elapsed time indicative of system malfunction, electronic switch means for conditioning said slug fall time means to provide said elapsed time voltage output, temperature responsive means for providing temperature signals in response to the temperature of the fluid and operatively connected with said electronic switch means for actuating said electronic switch means in response to said temperature signals, and circuit means connected with said electronic switch means for actuating said pump means and said valve means in response to switching signals from said electronic switch means.

4. A viscometer system operable with a process line carrying a fluid to be measured and comprising a vertically mounted fall tube, a slug located in said fall tube for movement therein between upper and lower positions, pump means for pumping fluid into said fall tube, valve means operable to a plurality of conditions for directing flow of fluid from said fall tube, conduit means connecting said pump means, said valve means, said fall tube and the process line, actuating means operably connected with said fall tube, said pump means, said valve means and said conduit means for automatically, sequentially placing the system in the following phases of operation: (a) purge phase in which said valve means is conditioned such that fluid is pumped by said pump means from the process line, through said fall tube, and through said valve means back to the process line, and (b) measure phase in which said pump means is deactuated and said slug can fall, first timing means providing a voltage output having a magnitude varying in accordance with the variations in the elapsed time for said slug to fall a selected distance, and second timing means responsive to an elapsed time of a preselected magnitude indicative of a malfunction for providing an alarm signal to said actuating means, said actuating means responsive to said alarm signal for placing and maintaining the system in said purge phase and preventing automatic sequencing out of said purge phase.

5. The viscometer system of claim 4 with said actuating means operable in response to completion of said purge phase for placing the system in a recirculate phase in which said valve means is conditioned such that fluid flow to the process line is blocked and fluid is recirculated in a fluid circuit comprising said fall tube, said valve means, said conduit means and said pump means, in said measure phase the remaining portions of the system being in said recirculate phase while said pump means is deactuated.

6. The viscometer system of claim 4 with said second timing means provided a second alarm signal for alerting an operator of the malfunction.

7. A viscometer system operable with a process line carrying a fluid to be measured and comprising a vertically mounted fall tube, a slug located in said fall tube for movement therein between upper and lower positions, pump means for pumping fluid into said fall tube, valve means operable to a plurality of conditions for directing flow of fluid from said fall tube, conduit means connecting said pump means, said valve means and said fall tube and the process line, actuating means operably connected with said fall tube, said pump means, said valve means and said conduit means for automatically, sequentially placing the system through repeated cycles in the following phases of operation:
(a) purge phase in which said valve means is conditioned such that fluid is pumped by said pump means from the process line, through said fall tube, and through said valve means back to the process line, and
(b) measure phase in which said pump means is deactuated and said slug can fall, timing means for providing a voltage output having a magnitude varying in accordance with the variations in the elapsed time for said slug to fall a selected distance, and recorder means for sequentially providing a plurality of recorded indications of the magnitudes of viscosity for a series of cycles as a function of the magnitudes of said voltage output and sample and hold means for maintaining the preceding one of said voltage output until a subsequent one of said voltage output whereby said indications will be maintained at the last measured said voltage output until the next one of said voltage output without returning to zero indication.

8. The viscometer system of claim 7 with said recorder means comprising a chart type recorder and further comprising electronic calibration means for selectively varying the span of said indication on said chart type recorder.

9. The viscometer system of claim 8 with said actuating means operable in response to completion of said purge phase for placing the system in a recirculate phase in which said valve means is conditioned such that fluid flow to the process line is blocked and fluid is recirculated in a fluid circuit comprising said fall tube, said valve means, said conduit means and said pump means, in said measure phase the remaining portions of the system being in said recirculate phase while said pump means is deactuated.

* * * * *

UNITED STATES PATENT AND TRADEMARK OFFICE
CERTIFICATE OF CORRECTION

PATENT NO. : 4,027,516
DATED : June 7, 1977
INVENTOR(S) : Samuel S. Ochodnicky and Frank J. Bianchi, Jr.

It is certified that error appears in the above-identified patent and that said Letters Patent are hereby corrected as shown below:

Column 2, line 3, delete "other" and substitute therefor --Other--.
Column 2, line 41, delete "by" second occurrence and substitute therefor --of--.
Column 3, line 9, delete "movable" and substitute therefor --movably--.
Column 3, line 10, delete "part" and substitute therefor --apart--.
Column 3, line 10, delete "59" and substitute therefor --50--.
Column 3, line 25, delete "(b)" second occurrence and substitute therefor --(c)--.
Column 3, line 37, delete "of" second occurrence and substitute therefor --by--.
Column 4, line 18, delete "+15" second occurrence and substitute therefor -- -15 --.
Column 4, line 29, delete "received" and substitute therefor --receives--.
Column 4, line 51, after "recorder" insert --18--.
Column 6, line 17, after "element" insert --148--.
Column 7, line 61, delete " 'quad" (close single quote) and substitute therefor -- ' quad-- (open single quote).
Column 8, line 5, delete "in" and substitute therefor --an--.

UNITED STATES PATENT AND TRADEMARK OFFICE
CERTIFICATE OF CORRECTION

PATENT NO. : 4,027,516
DATED : June 7, 1977
INVENTOR(S) : Samuel S. Ochodnicky and Frank J. Bianchi, Jr.

It is certified that error appears in the above-identified patent and that said Letters Patent are hereby corrected as shown below:

Column 8, line 48, delete "to" second occurrence and substitute therefor --in--.

Columns 11 and 12, Chart line 59, delete "R48 Resistor 200$\Omega$" and substitute therefor --R48 Resistor 220$\Omega$--.

Signed and Sealed this

Sixth Day of June 1978

[SEAL]

Attest:

RUTH C. MASON
*Attesting Officer*

DONALD W. BANNER
*Commissioner of Patents and Trademarks*